(12) United States Patent
Pologe

(10) Patent No.: US 6,754,515 B1
(45) Date of Patent: Jun. 22, 2004

(54) STABILIZATION OF NOISY OPTICAL SOURCES IN PHOTOPLETHYSMOGRAPHY

(75) Inventor: Jonas Alexander Pologe, Boulder, CO (US)

(73) Assignee: Kestrel Labs, Inc., Boulder, CO (US)

( * ) Notice: Subject to any disclaimer, the term of this patent is extended or adjusted under 35 U.S.C. 154(b) by 7 days.

(21) Appl. No.: 10/323,176

(22) Filed: Dec. 17, 2002

(51) Int. Cl.$^7$ .................................................. A61B 5/00
(52) U.S. Cl. ...................................... 600/322; 600/336
(58) Field of Search ............................... 600/310, 322, 600/323, 330, 336

(56) References Cited

U.S. PATENT DOCUMENTS

| | | | | |
|---|---|---|---|---|
| 5,553,615 A | * | 9/1996 | Carim et al. ................. | 600/324 |
| 5,830,132 A | * | 11/1998 | Robinson ..................... | 600/310 |
| 5,908,384 A | * | 6/1999 | West ........................... | 600/310 |
| 6,611,320 B1 | * | 8/2003 | Lindberg et al. ............. | 600/320 |

* cited by examiner

Primary Examiner—Eric F. Winakur

(57) ABSTRACT

A method and apparatus for photoplethysmographic measurements is disclosed. In this system light from a plurality of emitters is delivered to the tissue-under-test. A subset of one or more of the emitters is known to be quiet light sources with relatively stable output intensity levels and spectral contents. A second subset of one or more emitters is known to be relatively noisy light sources with output intensity levels that fluctuate over time. The use of noisy light sources may be necessary for the photoplethysmographic measurements due to favorable spectral output characteristics such as narrow spectral bandwidth or desirable center wavelengths for the measurement of the hemodynamic parameters or analytes of interest. This invention utilizes the quiet light sources to enable the use of noisy light sources without the loss in accuracy or precision of analyte measurement that would otherwise typically be associated with the use of noisy light sources in the design and use of a photoplethysmographic instrument.

21 Claims, 7 Drawing Sheets

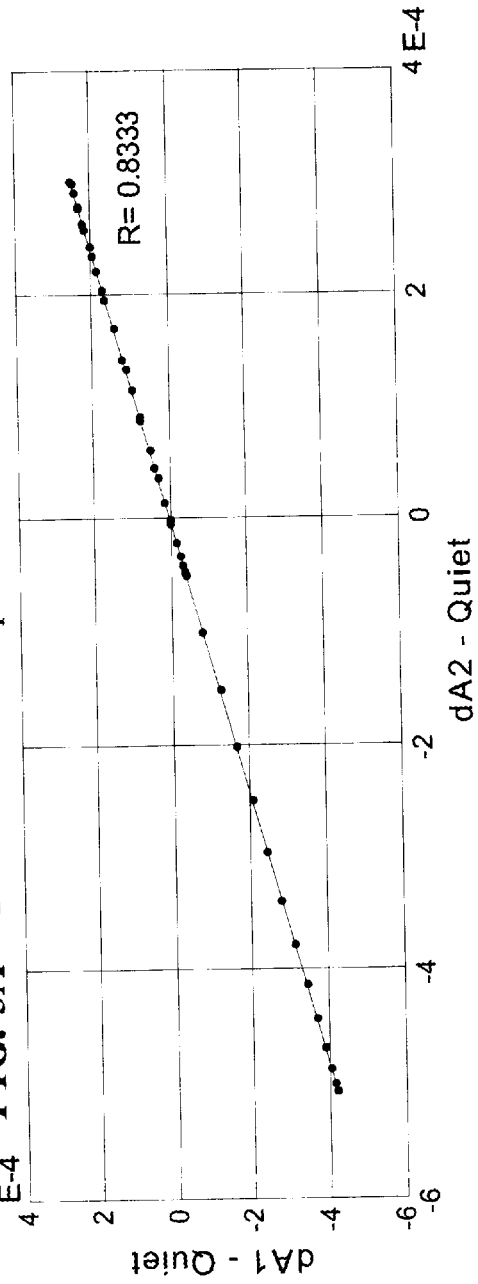
FIG. 5A Differential Absorption: Channel 1 vs Channel 2
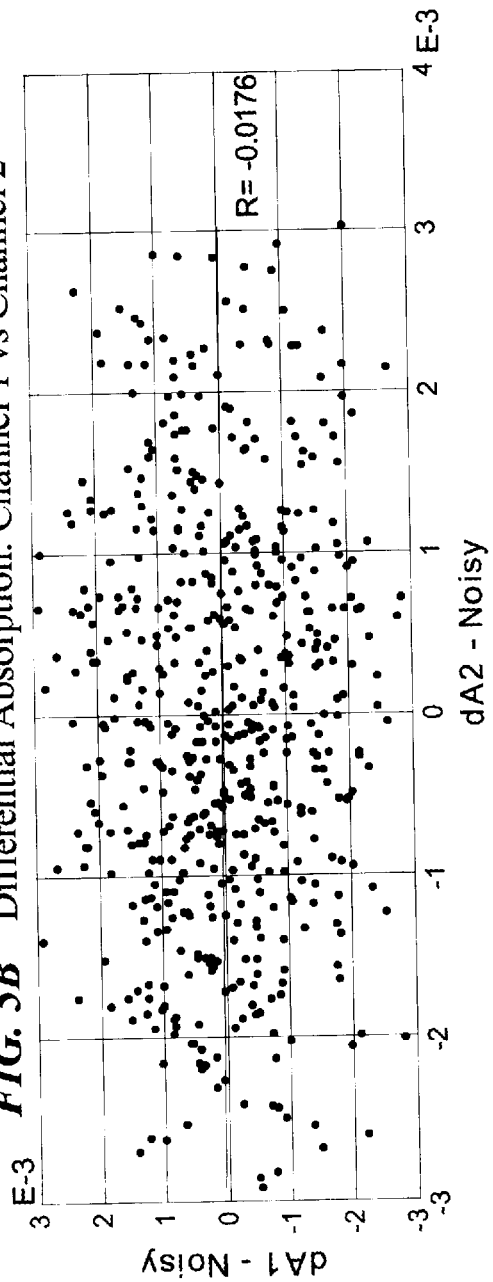
FIG. 5B Differential Absorption: Channel 1 vs Channel 2

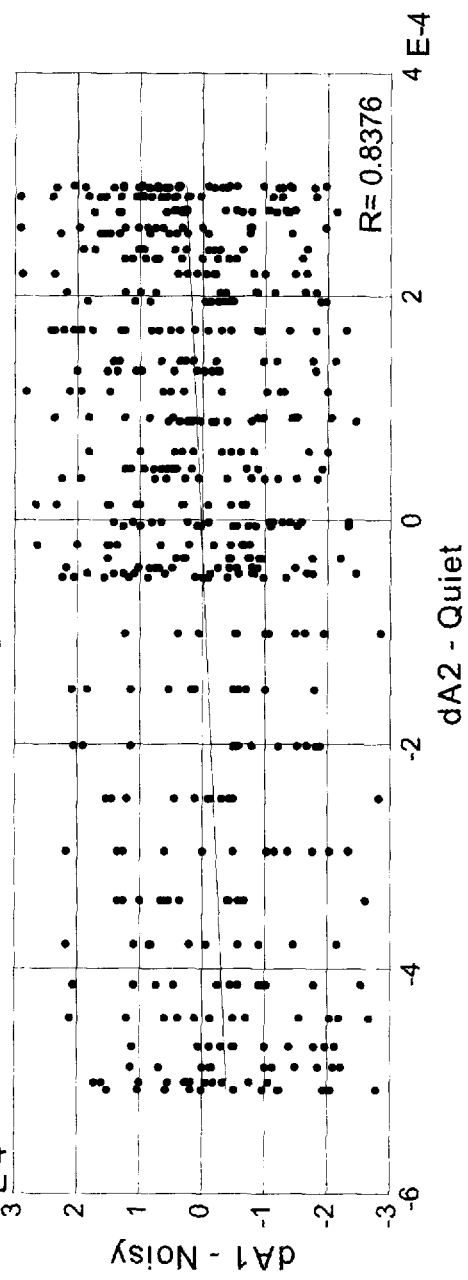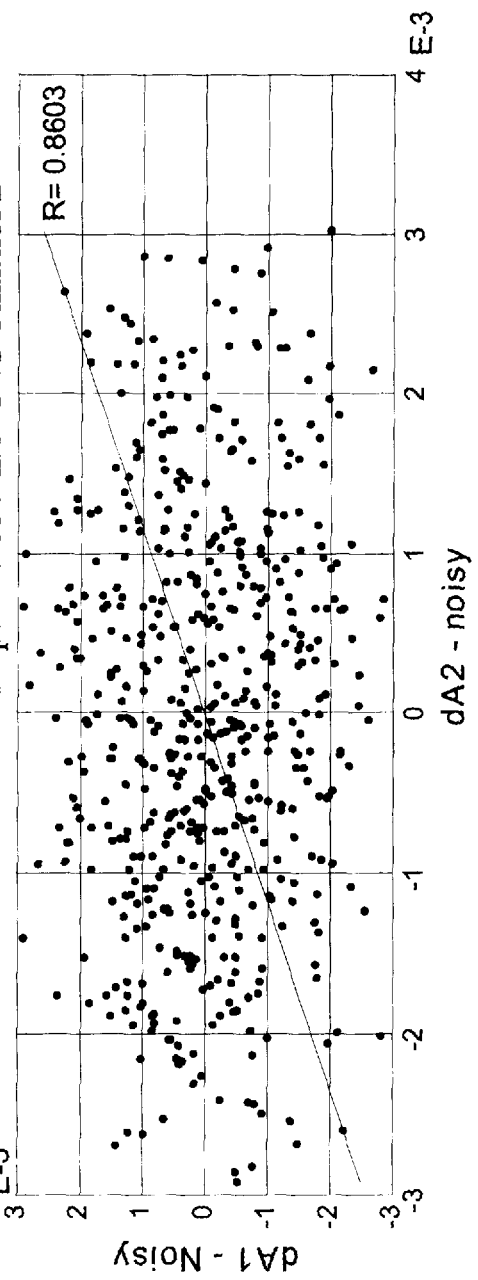

STABILIZATION OF NOISY OPTICAL SOURCES IN PHOTOPLETHYSMOGRAPHY

FIELD OF THE INVENTION

The present invention relates in general to a method and apparatus for eliminating the effects of noise inherent in certain optical sources used in photoplethysmographic measurements.

BACKGROUND OF THE INVENTION

In the science of photoplethysmography, light is used to illuminate or trans-illuminate living tissue for the purpose of measuring blood analytes or other hemodynamic or tissue properties. In this monitoring modality light is injected into living tissue and a portion of the light which is not absorbed by the tissues, or scattered in some other direction, is detected a short distance from the entry point. The detected light is converted into an electronic signal that is indicative of the received light signal from the tissue. This electronic signal is then used to calculate physiologic parameters such as arterial blood oxygen saturation and hemodynamic variables such as heart rate, cardiac output, or tissue perfusion. Among the blood analytes that may be measured by photoplethysmography are the various species of hemoglobin, including the percentages of oxyhemoglobin, carboxyhemoglobin, methemoglobin, and reduced hemoglobin in the arterial blood. A device which detects and processes photoplethysmographic signals to measure the levels of various blood analytes and hemodynamic parameters is referred to as a photoplethysmographic apparatus, device, or instrument. Typically these instruments also include, and control, the light sources or emitters used to generate the light that illuminates the tissue.

The first widespread commercial use of photoplethysmography in medicine was in the pulse oximeter, a device designed to measure arterial blood oxygen saturation. To make these measurements, two different bands of light must be used, with each light band possessing a unique spectral content. Each spectral band, or light band, is typically referred to by the center wavelength, or sometimes by the peak wavelength, of the given band. In pulse oximetry two different light emitting diodes (LEDs) are typically used to generate the sensing light, one with a center, or peak, wavelength near 660 nanometers (nm) and a second with a center, or peak, wavelength near 940 nm.

Light from each LED light source, or emitter, is passed into the tissue-under-test, usually a finger, earlobe, or other relatively thin, well-perfused tissue sample. After passing some distance through the tissue-under-test, a portion of the light not absorbed by the tissue or scattered in some other direction is collected by a photodetector and converted into electronic signals that are directly proportional to the received light signals. The channels, or electronic signals from each of the different light sources, are kept separated through the use of any one of a number of different well-published techniques, including but not limited to, time-division multiplexing or frequency-division multiplexing.

The signals received from the tissue are referred to as photoplethysmographic signals. These signals consist of a small pulsatile component and a rather large constant component that changes slowly over time when compared with the pulsatile component of the signal. The pulsatile component of the photoplethysmographic signal is created by the pulsation of the blood in the tissue-under-test. When the heart contracts, it pushes blood out of the heart and into the peripheral tissues. This increases the optical density of the tissue located between the emitter and detector elements of the sensor, which decreases the amplitude of the received optical signals. As the heart relaxes and refills with blood, the optical density of the tissue-under-test decreases, and the received signal amplitude increases. The comparatively constant component of the photoplethysmographic signal is often referred to as the DC component of the signal, and the pulsatile component of the photoplethysmographic signal is often referred to as the AC component of the signal.

The photoplethysmographic signals are processed to obtain a measurement of the oxygen saturation in the arterial blood. This can be done in a number of different ways but all require mathematically relating the amplitude of the photoplethysmographic signals from each of the two channels to the arterial oxygen saturation.

In conventional pulse oximetry the instrument has only two channels, one associated with each emitter or light source used. With only two channels, only two blood analytes can be measured. Conventional pulse oximetry makes the mathematical assumption that there are primarily only two types of blood analytes in the arterial blood, oxyhemoglobin and reduced hemoglobin.

In order to measure only the arterial oxygen saturation, the pulse oximeter makes use of both the pulsatile component and the DC component of the photoplethysmographic signals. Because any pulsation of the venous system or capillaries is small by comparison to the arterial pulsation, changes in the amplitude of the photoplethysmographic signals will be dominated by the arterial pulsation. Note that the photoplethysmographic signals can be severely distorted by artifacts such as patient motion or electrocautery but elimination of these sources of artifacts is not the focus of this patent and will not be specifically addressed herein.

The amplitude of the pulsatile component of these photoplethysmographic signals can be extremely small. It is not uncommon for the percent modulation, or the peak-to-peak amplitude of the pulsatile portion divided by the constant portion, to be less than one part in one thousand, or 0.1%. Thus it is crucial that extremely quiet light sources are used to generate the signals for probing the tissue-under-test. This is necessary because any intensity noise in the light source that is within the frequency range of the passband of the photoplethysmographic device, or which can alias into its passband, will show up in the received photoplethysmographic signals and corrupt the desired measurements. Thus to allow for accurate and precise photoplethysmographic measurements, the light sources should be extremely quiet (also referred to as "noise free") or a means must be found to eliminate the light noise from the received signals.

Since the inception of photoplethysmography, this monitoring modality has been used to detect more and more different parameters. For example, a device was disclosed in Jarman et al U.S. Pat. No. 5,983,122 that is capable of measuring the percentages of four different analytes in the arterial blood, including oxyhemoglobin, carboxyhemoglobin, methemoglobin, and reduced hemoglobin.

As the number of different parameters measured by photoplethysmography increases, so too does the number of different bands of light required to make the measurements. Further, because a fairly high intensity of light over a fairly narrow spectral range is needed for these measurements, it has been found that the most successful sources of light for these measurements have been discrete, narrow-band emitters such as LEDs or laser diodes. These types of light sources are typically used because broadband sources (in conjunction with filters or a diffraction grating to obtain the required spectral bands) produce too little energy over the desired narrow spectral bandwidths to provide sufficient signal amplitude for photoplethysmographic measurements.

LEDs are inherently very quiet light sources but do not have a sufficiently narrow spectral bandwidth for use at all of the required center wavelengths. Conventional edge-emitting diode lasers provide the necessary narrow bandwidth but can be quiet noisy. For example, in a time-division multiplexed system, the intensity of the light emitted by a laser diode can vary from pulse to pulse, or can even jump almost instantaneously during any given pulse. These intensity variations can easily be large enough to prevent the measurement of the desired blood analytes to clinically-acceptable accuracy and precision levels. While not all types of laser diodes are noisy, often the photoplethysmographic instrument designer must use an inherently noisy light source if it is the only one available that has the required bandwidth and center wavelength needed for measurement of the desired blood analytes.

Vertical cavity surface-emitting lasers (VCSELs) can be very quiet but are generally unavailable at wavelengths shorter than about 800 nm. Thus for the shorter wavelengths it is often necessary to use an inherently noisy edge-emitting laser diode. Unfortunately, the noise levels in this type of laser have made the development of commercially viable photoplethysmographic devices based on these types of light sources impossible as the magnitude of the laser noise simply introduces too much error into the desired analyte measurements.

One of the reasons for the noise in the output of edge-emitting lasers is that once the laser is energized, the semiconductor junction temperature increases and the length of the laser cavity begins to change due to thermal expansion of the semiconductor die. If the cavity length changes, the original lasing wavelength of the device will no longer be the optimal wavelength for the new cavity length, because it will not fit inside the cavity with a whole number of wave periods. When this occurs a new lasing wavelength will become dominant within the cavity, essentially "crowding out" the wavelength that was previously lasing. When this transition occurs there is also a small instantaneous change in the output optical power. It is these sudden changes that cause the noise that is seen at the output of these noisy light sources.

Mode hopping is only one source of light intensity noise. Other types of emitters can introduce noise as well. Tungsten light sources, for example, can be noisy just due to movement of the tungsten filament in the bulb. This type of broadband light source has been used in the past in photoplethysmographic instrumentation. To obtain the necessary spectral content the light from this element can be filtered by narrowband filters or spectrally dispersed by a diffraction grating. In either case the photoplethysmographic signals derived from these types of light sources can have high enough noise levels to cause large inaccuracies in the desired measurements.

It is important to recognize that as the number of blood analytes to be measured by a single photoplethysmographic device increases, the number of light sources (or at least the number of channels) also increases, and the effects of even very small amounts of noise are more and more noticeable. This is directly attributable to the fact that each photoplethysmographic signal, originating from each emitter, is simultaneously reading multiple blood analytes. As a result the light levels of each channel must be read with higher accuracy, and the detrimental effect of any given amount of noise on that channel is greater.

It has long been recognized by the medical community that conventional pulse oximetry is inaccurate in the presence of additional species of hemoglobin beside oxyhemoglobin and reduced hemoglobin. Steven J Barker, M.D., in a 1987 article entitled "The Effect of Carbon Monoxide Inhalation on Pulse Oximetry and Transcutaneous P02," published in the journal *Anesthesiology*, explained the errors in pulse oximetry caused by elevated levels of carboxyhemoglobin. Two years later in another *Anesthesiology* article entitled "Effects of Methemoglobinemia on Pulse Oximetry and Mixed Venous Oximetry," Barker defined the errors in pulse oximetry readings caused by elevated methemoglobin levels. These articles, along with numerous case studies, make clear the long-standing need for a pulse oximeter capable of measuring all four primary species of hemoglobin. Additionally, the Pologe patent, U.S. Pat. No. 5,891,022, from 1999, the Pologe et al patent, U.S. Pat. No. 5,790,729, from 1988, and the Barthelemy et al patent U.S. Pat. No. 5,413,100 from 1995, all recognized the need for the use of multiple laser diodes to measure the additional blood analytes discussed above. These patents demonstrate the understanding that multiple laser diode based emitters, with carefully selected center wavelengths, must be combined to create an instrument capable of measuring the four primary hemoglobin species.

Despite the long-standing recognition of the clinical need for this type of instrument no photoplethysmographic device exists to measure these four species of hemoglobin. The primary problem that continues to prevent these ideas from developing into a commercially viable instrument is the high noise level inherent in most commercially available laser diodes.

In the design of a multi-parameter photoplethysmographic device, it is necessary to use emitters that have narrow bandwidths and mathematically-selected center wavelengths to allow for the measurement of the desired blood analytes. This can necessitate the use of inherently noisy light sources. Unfortunately these noisy sources distort the very photoplethysmographic signals that are necessary for these measurements. Thus it is necessary to find a way to utilize these noisy sources and still make analyte measurements to the required levels of accuracy and precision.

BRIEF SUMMARY OF THE INVENTION

In the science of photoplethysmography, light is used to illuminate, or trans-illuminate, tissue for the purpose of measuring blood analytes or hemodynamic properties or parameters. In making these measurements it can become necessary to use light from a number of different types of sources including, but not limited to, incandescent bulbs, light-emitting diodes (LEDs), and lasers. The use of laser light sources becomes necessary when very narrow spectral bandwidth (narrow band) light is required to make possible the accurate photoplethysmographic measurement of certain specific blood analytes or the simultaneous measurement of a number of blood analytes such as oxyhemoglobin, reduced hemoglobin, carboxyhemoglobin, and methemoglobin. It is the purpose of this invention to allow accurate photoplethysmographic measurements using inherently noisy light sources that otherwise have desirable optical properties, including precisely tunable or selectable center wavelengths and high output intensity over a narrow spectral bandwidth.

This invention combines the use of at least one relatively quiet optical source with any number of noisier optical sources. For example, in one embodiment of this invention, a light emitting diode (LED) is used in combination with a number of edge-emitting laser diodes to provide all of the required spectral bands (of light) necessary to measure the target analytes. In this example, the targeted blood analytes include oxyhemoglobin, reduced hemoglobin, carboxyhemoglobin, and methemoglobin. The laser diodes provide high-intensity, narrowband, albeit relatively noisy, outputs at the center wavelengths that are required to allow measurement of these blood analytes. The LED provides an optically stable (also referred to as quiet or clean) output that is used, at least in part, to minimize the effect of the noise that is inherent in the laser sources.

As any noise in the input light sources becomes noise in the photoplethysmographic waveforms that are received by the photodetector, this intensity noise distorts the waveforms used to determine the blood analyte levels and can dramatically increase the inaccuracy of the measurements. Note also that if there is a reduction in the patient's perfusion at the sensor site (the position on the tissue where the sensing light enters and is received from the tissue-under-test), there is a dramatic increase in the errors in the analyte measurements because although there is a fixed amount of intensity noise inherent in the light sources, this noise becomes larger in proportion to the pulsatile component of the photoplethysmographic waveform. This invention provides a way to utilize a quiet (or relatively quiet) light source to eliminate or at least minimize the effects of light intensity noise generated by inherently noisy (or relatively noisy) light sources in a photoplethysmographic device.

In this invention a quiet source, in this example the LED, provides a quiet photoplethysmographic waveform which acts as a "template" that is used to eliminate, or at least minimize, the noise inherent in the photoplethysmographic waveforms generated by the noisier sources.

In an ideal photoplethysmographic device, different light sources emit light that is incident on the tissue-under-test through essentially the same small output aperture. The light from each source then ideally passes through the tissue traversing the same optical path. This generates a set of photoplethysmographic waveforms, one for each emitter, which are received by the detector, typically a silicon photodiode or equivalently any type of photodetector that is sensitive to the wavelengths of light emitted by the sources. The light signals from the different sources are kept separate from each other by any one of a number of different electronic schemes such as time-division multiplexing, where only one light source is turned on at a time and all the emitters are cycled through in rapid succession. Another scheme sometimes used is frequency-division multiplexing, where each light source is modulated at a different frequency. These are well-defined techniques in the art of electronics in general which have both been extensively used in the past in photoplethysmography, and will thus not be further explained herein.

In a perfectly noise free system, each photoplethysmographic waveform can be mapped into any other waveform by nonlinear amplitude scaling. In photoplethysmography the transform that scales one waveform into another is known; what is not known is the magnitude of the scaling that is required, as this depends on the level of the blood analytes and other absorbers in the tissue-under-test.

If the intensity noise generated by the noisy light sources is random in nature, a statistical least squares fit of the waveform from the quiet light source will allow the correct selection of the scale factors required to create a noise free (or at least quiet) version of the waveform data originating from any of the noisy light sources. This set of quiet photoplethysmographic waveforms can then be used in the calculation of the various desired blood analytes or hemodynamic variables. In this way the clean (or quiet) photoplethysmographic waveform has acted as a template to provide the correct waveshape for the noisy waveforms. This allows the use of noisy sources in the photoplethysmographic measurements, while eliminating or at least minimizing the error that would have been generated by the intensity noise.

The quiet light source used in the instrument may serve a dual role. It may provide the quiet light source for minimizing the effects of the noise in the noisy channels and it may also be one of the selected center wavelengths, or spectral bands, used for the analyte or hemodynamic measurements. The advantage of this is that the dual use of the quiet channels reduces the number of light sources required for the system, thus minimizing the complexity and cost of the instrument. In reduction to practice at the current time, the optimal light sources for the quiet channels will typically be either LEDs or VCSELs. The term "channel" is used to indicate those data associated with the light out of the tissue-under-test, picked up by the sensor photodetector, originating from any given emitter. These data can be in the form of light levels, current levels, voltage levels, or mathematical values after conversion of the analog signals to digital values.

In this patent the term "template" is used in conjunction with any technique in which the data from the quiet channel (or channels) is utilized to minimize the effects of the noise in the noisy channels. The template is the clean, or relatively noise free, photoplethysmographic data. The conceptually simplest technique, where the waveshape of the quiet channel is scaled to fit the data from the noisy channels, is explained above. This is just one of a number of ways of performing the noise elimination using a known clean channel. A second method, utilizing linear regression of differential absorption measurements, is described in detail below. While the two techniques are mathematically different, they both use the quiet channels to clean up the noisy ones, and therefore the quiet channel is still considered to be a template.

BRIEF DESCRIPTION OF THE DRAWINGS

FIG. 5 Shows two separate plots of differential absorption for Channel 1 verses Channel 2. The spectral content for Channel 1 in both plots and for Channel 2 in both plots is identical. In FIG. 5A, however, the data are from two quiet channels, and in FIG. 5B the data are from two noisy channels. Also shown is the linear regression line for the displayed data and the "R" value (slope) of the regression line.

FIG. 6 again shows two separate plots of differential absorption for Channel 1 verses Channel 2. In these plots, however, the apparatus and method of this invention are used to calculate the regression lines and slopes. These regression lines and their associated slopes (R values) are displayed.

DETAILED DESCRIPTION OF THE INVENTION

Prior to this invention all emitters used for photoplethysmographic devices have been selected to provide bands of light with the correct spectral content to probe the tissue-under-test for the analytes of interest. In conventional pulse oximetry, for example, the emitters typically consist of two light emitting diodes (LEDs) that are used to probe the tissue-under-test for the two analytes of interest, oxyhemoglobin (O2Hb) and reduced hemoglobin (RHb). In one of the first photoplethysmographic devices, the Minolta/Marquest Oxygen Saturation Monitor SM-32 pulse oximeter, a broadband light source was used, and the received light was split into two separate paths and passed through two separate interference filters to generate the two bands needed to analyze the tissue for the O2Hb level to be displayed. In the present invention one or more relatively quiet emitters are specifically included for the purpose of removing or eliminating the noise inherent in one or more of the other relatively noisy emitters in the device.

In the current preferred embodiment of this invention, it is desired to measure four separate blood analytes, O2Hb, RHb, carboxyhemoglobin (COHb) and methemoglobin (metHb), by photoplethysmography. To accomplish this measurement a minimum of four spectral bands are required. While this light could be generated by a broadband light source split into the desired components through the use of a diffraction grating or optical filters, in this embodiment four individual edge-emitting laser diodes are utilized. These laser diodes are inherently noisy light sources and this intensity noise can make the measurement of the desired analytes, from the resultant photoplethysmographic waveforms, highly inaccurate. Thus in this invention one or more quiet light sources are included to provide stable, relatively noise-free, photoplethysmographic data that is subsequently used to "clean up" the noisy photoplethysmographic data (or calculations or measurements made utilizing these data) originating from the noisier light sources.

Figure 1:
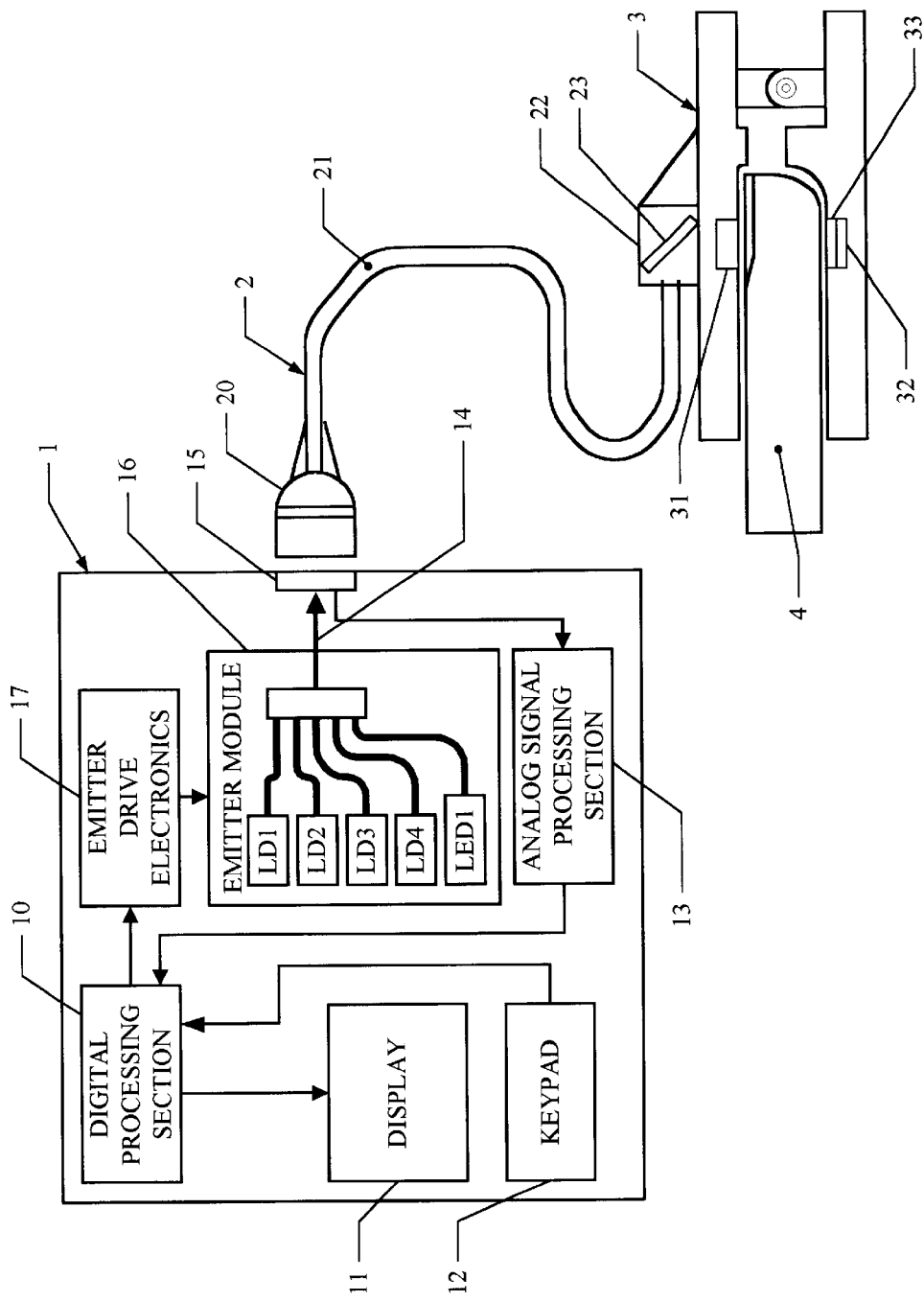
FIG. 1 is a block diagram of the photoplethysmographic instrument and sensor showing the control flow, front panel connector, cable connector, sensor cable, and sensor. The instrument block diagram also specifically includes a schematic representation of the Emitter Module which houses a plurality of one or more noisy light sources and plurality of one or more relatively quiet light sources.

FIG. 1 shows a block diagram of the Photoplethysmographic Instrument 1 along with the Sensor Cable Connector 20, Sensor Cable 2, and Sensor 3, necessary for photoplethysmographic measurement, as well as a finger representing the Tissue-Under-Test 4. Internal to the instrument in this preferred embodiment are a number of different sections. The Display 11 and the Keypad 12 provide the principle user interface. The Keypad 12 allows for input from the user to set alarm limits on the various parameters and analytes being monitored, control speaker (not shown) volume, silence alarms, and control other user-selectable features of the device. The Display 11 provides a visual representation of the measured blood analytes and hemodynamic parameters as well as, in this preferred embodiment, a view of a few seconds of one of the photoplethysmographic waveforms. This view of the waveform assists the end user in obtaining good sensor placement and physiological signal strength to allow for the best possible measurements.

The Digital Processing Section 10 controls the information flow throughout the instrument. It typically consists of a processor, such as a microprocessor, in combination with the necessary memory elements and standard control circuitry. The memory elements typically contain the software program that runs the instrument and controls the processing of the input photoplethysmographic data. This section also monitors the Keypad 12 for input and sends output values to the Display 11 or to digital or analog data output ports (not shown). It also provides the control signals to turn on and off the Emitter Drive Electronics 17.

The Emitter Drive Electronics 17 generate the drive signals to control the emitters in Emitter Module 16. These drive signals are time-division multiplexed, in this embodiment; that is, each light source is turned on for a predetermined amount of time and then turned off. This on/off cycle is repeated with other light sources in the device until all light sources have been energized, and then the cycle is repeated. There is also a predetermined time period in each cycle when all light sources are turned off to allow for elimination of background light levels. The light sources indicated in the drawing by LD1 through LD4 are four edge-emitting laser diodes, each with a different spectral content and center wavelength. These light sources generate the four required spectral bands needed to measure the four analytes of interest. These are the "noisy" light sources in this particular embodiment. While edge-emitting laser diodes are the noisy light sources used in this particular embodiment, the method and apparatus of this invention can effectively minimize any relatively random noise in the intensity of the output light from the emitters.

To minimize the noise, or the effects of the noise, caused by the noisy light sources on the photoplethysmographic measurements, at least one quiet light source is required. In the context of this invention a "quiet" light source is one that has measurably less intensity noise than the noisy sources and is specifically used to minimize the effects of the noise on the photoplethysmographic measurements. In the embodiment shown in FIG. 1, the quiet light source is designated by LED1 in Emitter Module 16. When energized by stable emitter drive circuitry, the LED source or sources can have less than one tenth the peak-to-peak amplitude of the intensity noise found on the outputs of the edge-emitting laser sources, even if this noise is expressed as a percentage of the maximum output intensity. This low noise level makes the LED source acceptable for the method and apparatus presented herein whereby a quiet light source is used to extract clean signals from inherently noisy optical sources.

Once the light signals are generated, they are directed into a common fiber, a fiber bundle, or some other form of Light Guide 14 for transmission to the Sensor 3, and then on to the Tissue-Under-Test 4. In this embodiment all of the light sources are located inside the Photoplethysmographic Instrument 1. However the exact location of the light sources relative to the tissue-under-test is not relevant to this invention. In most conventional pulse oximeters currently on the market, the light sources are positioned within a sensor housing.

The electronic signals representative of the photoplethysmographic data return to the Photoplethysmographic Instrument 1 and are routed to the Analog Processing Section 13. The Analog Processing Section 13 typically performs various functions to condition the electronic signals before sending them back to the Digital Processing Section 10. These functions include: filtering out unwanted frequency content; amplifying the photoplethysmographic data to a range optimal for analog to digital conversion; demultiplexing the electronic signals back into individual channels, i.e. one channel for each light source or unique spectral band; simultaneous sample and hold of the data from all channels (that is the periodic sampling of all photoplethysmographic waveforms, or channels, simultaneously), and finally conversion of the sampled data from the analog to the digital domain.

The Instrument Sensor Connector 15 provides the interface between the Photoplethysmographic Instrument 1 and the Sensor Cable 2. This connector passes the optical signals generated by the Emitter Module 14 that must be delivered to the Sensor 3 and passes the electronic signals returning from the Sensor 3 that must be routed to the Analog Signal Processing Section 13. In the preferred embodiment, the Instrument Sensor Connector 15 and Sensor Cable 2 are of hybrid design, capable of handling both optical and electrical signals. It is equally permissible to use separate connectors and cables to handle separate optical and electrical signals.

The Sensor Cable Connector 20 mates with the Sensor Connector 15. The electrical and optical signals are passed through the hybrid Sensor Cable 2 via a mixture of Wires and Light Guides 21 contained within the cable. The wires pass from the Sensor Cable 2 into the Sensor 3 and terminate at the Detector 32, which is typically a silicon photodiode. The light guides terminate in the Mirror Housing 22 and the optical signals exiting the light guides are then incident on the Mirror 23 and reflected toward and through the Emitter Aperture 31 to be incident on the Tissue-Under-Test 4. The light signals then pass some distance through the Tissue-Under-Test 4. The light not absorbed by the chromophores in the tissue, or scattered away from the Exit Aperture 33, is then incident on the Detector 32 intensity of the light received.

It is crucial in photoplethysmographic instrumentation that all light incident on the tissue-under-test enters the tissue through the same small aperture regardless of which emitter generated the light. The optical and geometric configuration of the Sensor 3 must be designed such that this condition is met. In the embodiment shown in FIG. 1, the Mirror 23 reflects the light generated by the emitter set housed in the Photoplethysmographic Instrument 1, and transmitted to the Sensor 3 via the Light Guide 21, towards the Emitter Aperture 31. The Mirror 23 also allows for the light output from the Light Guide 21 to spread out, fully filling the Emitter Aperture 31, and therefore co-locating the light from all sources. With this design, the criterion that all light sources enter the Tissue-Under-Test 4 through the same aperture is met. This is necessary to ensure that the path the light takes through the Tissue-Under-Test 4 to the Exit Aperture 33 is essentially identical for all emitters.

This is only one potential instrument and sensor configuration. As mentioned earlier, the emitters can be housed in a number of different locations including: inside the instrument; in the sensor; or at some intermediate position along the length of the sensor cable. The sensor itself can come in many different forms including sensors specifically configured for positioning the optical and electrical elements on the finger, ear, toes, bridge of the nose, across the nares, infant feet, or any place where the tissue thickness is not too great. If the thickness of the tissue-under-test is too large, insufficient light will pass from the Emitter Aperture 31 to the Detector 32 and the received signal strength will be too for photoplethysmographic measurement. Alternatively, the sensor can be designed to pass light from one point to another along essentially the same surface. Such sensors are typically referred to as "reflectance" sensors and can be positioned on the face at the cheek or the forehead or on other fairly flat areas that have sufficient surface perfusion to provide an adequate photoplethysmographic signal.

Figure 2:
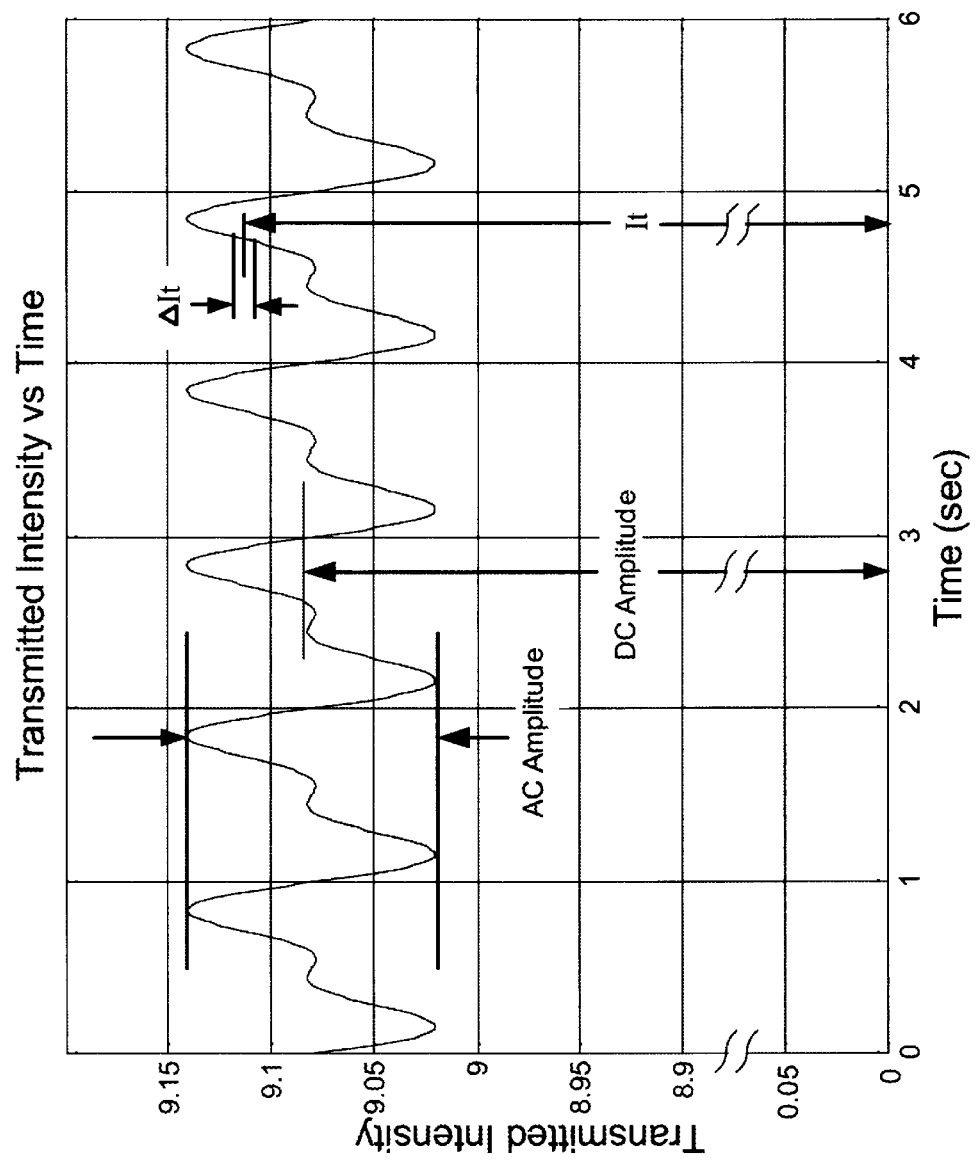
FIG. 2 is a plot of a photoplethysmographic waveform as a function of time.

To understand this invention, one must understand how the photoplethysmographic data are manipulated as well as the apparatus from FIG. 1, previously described. FIG. 2 is a plot of a typical photoplethysmographic signal. The data are plotted in the form of transmitted intensity as a function of time. For clarity only one waveform is shown, but for any given instrument there will be one waveform for every channel or emitter used. Note that the Y-axis is relative only, and the top of the waveform is shown, greatly magnified, by displaying the data on a scale from about 8.90 to 9.15. This makes it possible to see the small pulsatile, or AC, component of the signal. As shown, if the AC amplitude is the peak-to-peak amplitude of the waveform, and the DC amplitude is the root mean squared amplitude of the waveform, then the percent modulation of the waveform can be expressed as in Equation 1.

$$\% \, Mod = \frac{AC}{DC} \qquad \text{Equation 1}$$

For the photoplethysmographic waveform shown in FIG. 2, the percent modulation is a little over 1%. Percent modulation for a photoplethysmographic waveform, generated on a finger with narrowband light centered around 900 nanometers (nm), can range from over 10% to less than 0.1%. Considering that such a wide range of percent modulations can be present in a clinical setting, it is important to note that a noise level which might be considered trivial when compared to a photoplethysmographic signal with 10% modulation could completely bury a signal that has only 0.1% modulation. The potential for extremely low percent modulation signals, caused by low tissue perfusion at the sensor site in the tissue-under-test, is one reason why even relatively low levels of intensity noise in the emitters is so detrimental to measurement accuracy. Low tissue perfusion is a fairly common event, if not almost the norm, in photoplethysmographic monitoring. It can be caused by shock, low blood pressure, or environmental conditions such as a cold examining room, where peripheral circulation is minimized to maintain core body temperature. From a clinical standpoint, the lower the tissue perfusion, the sicker the patient might be, and the more important it is that the photoplethysmographic monitor provide accurate readings.

Differential absorption is defined as in Equation 2

$$dA_\lambda = \frac{dIt}{It} \approx \frac{\Delta It}{It} \qquad \text{Equation 2}$$

In words, Equation 2 states that the differential absorption of light, at any given wavelength, is defined as a differential change in transmitted intensity, dIt, divided by the total transmitted intensity, It. The equivalence operator in Equation 2 denotes that dA can be approximated by a very small change in the intensity of the photoplethysmographic waveform, shown in FIG. 2 as ΔIt, divided by the total intensity, shown in FIG. 2 as It. For a multi-channel or multi-emitter system the dAs from each channel are measured simultaneously.

Figure 3:
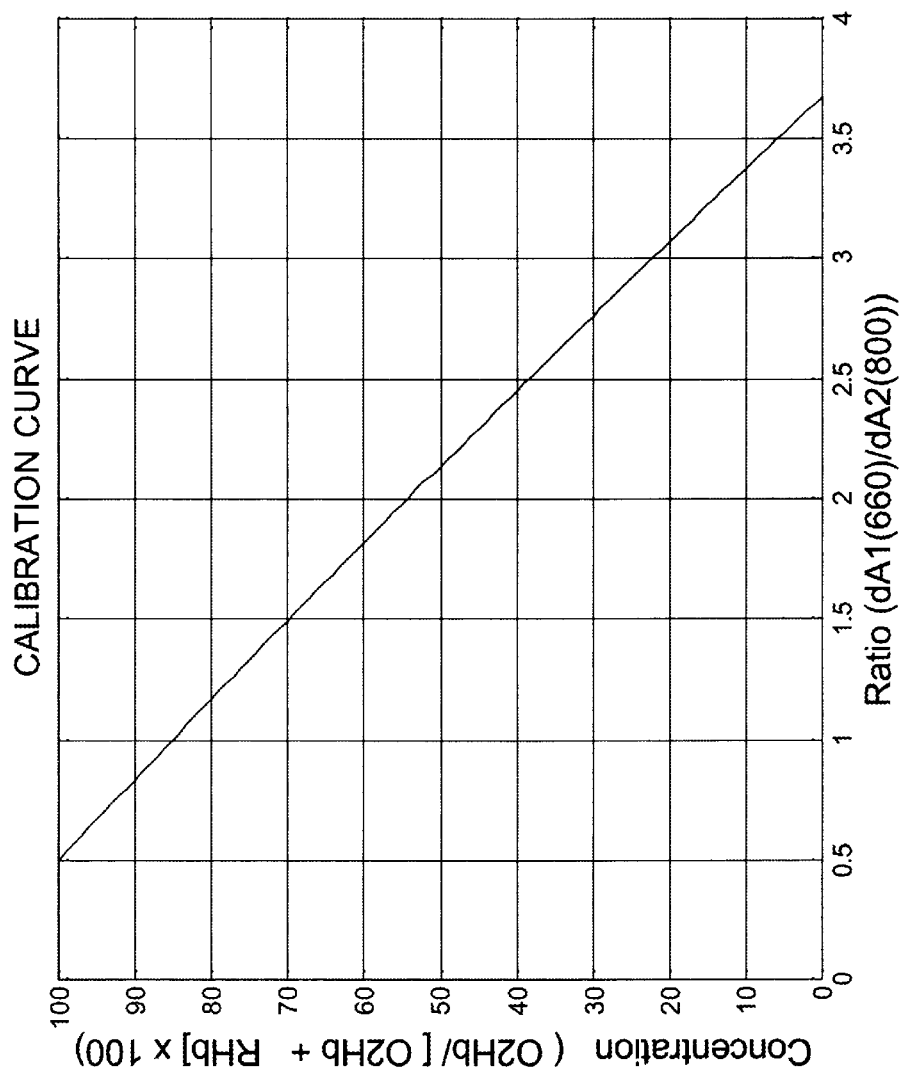
FIG. 3 is a graph of the calibration curve for a two channel photoplethysmographic device designed to measure oxygen saturation (O2Hb) using two emitters (or two light bands), one centered at approximately 660 nm and a second one centered at about 800 nm.

It is common in the art of pulse oximetry to develop a calibration curve that relates the differential absorptions, measured simultaneously at two different wavelengths, to the analyte of interest. In conventional pulse oximetry, the analyte of interest is oxyhemoglobin (O2Hb). FIG. 3 is a plot of just such a calibration curve. It shows the relationship between the oxygen saturation, O2Hb, and the ratio of differential absorptions (dAs) of light centered at two different wavelengths, 660 nm and 800 nm. For example, a ratio of these dAs equal to 1 relates to an O2Hb of approximately 85%. Written mathematically, in Equation 3, it is clear that O2Hb is a function of $dA_{660}$ and $dA_{800}$.

$$O2Hb = f(dA_{660}, dA_{800}) \qquad \text{Equation 3}$$

Given the functional relationship between O2Hb and the dA values, it should be obvious that the more accurately the dA values can be measured, the more accurately O2Hb can be calculated. Because the dA values are derived from the photoplethysmographic waveforms, as shown in FIG. 2, the initial goal must be accurate and noise free measurement of these waveforms.

Figure 4:
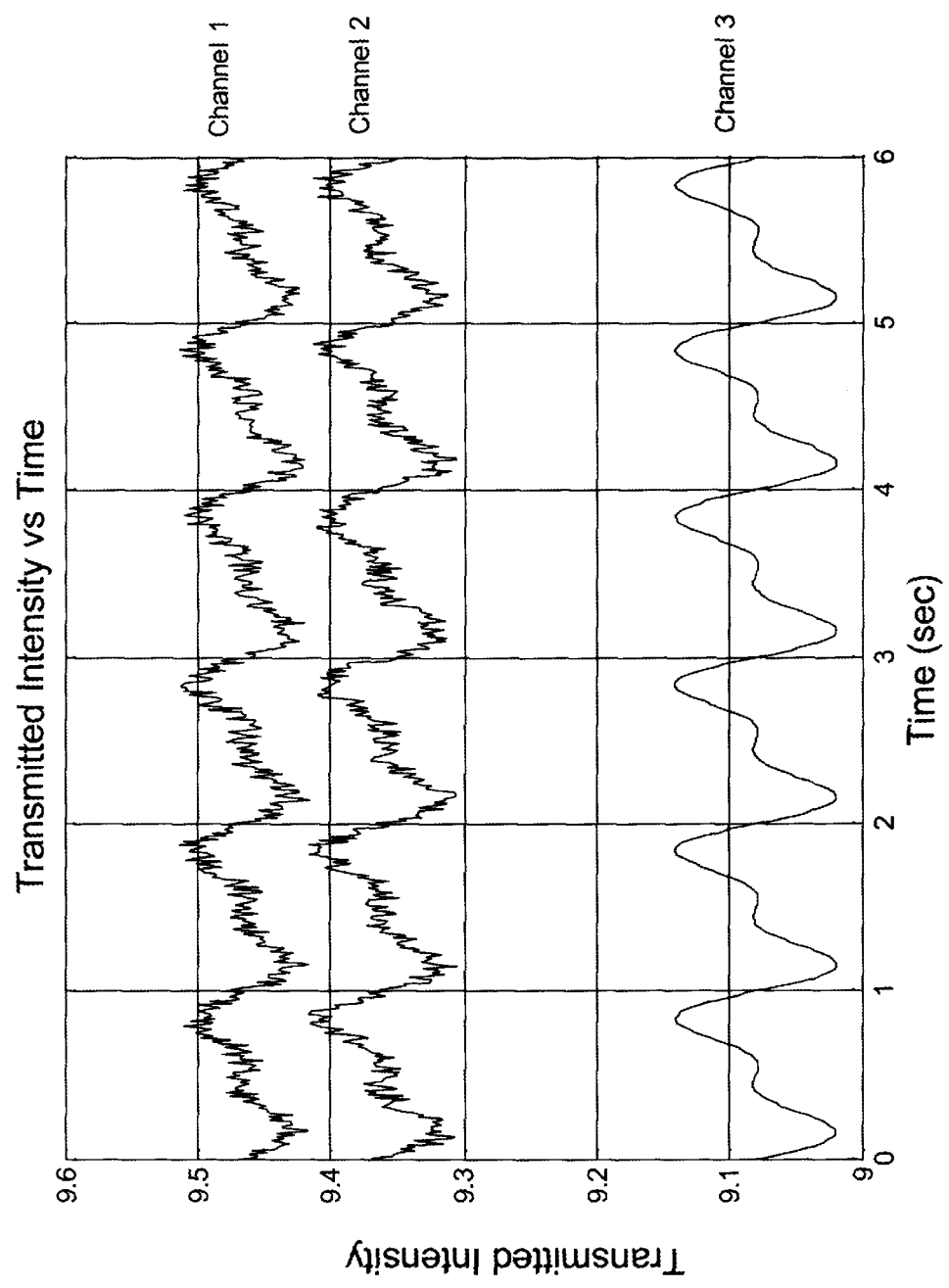
FIG. 4 is a graph showing three channels of photoplethysmographic data collected simultaneously from the same tissue-under-test. Channels 1 and 2 originate from a relatively noisy light source and channel 3 originates from a relatively quiet light source.

FIG. 4 shows the waveforms from a three-channel photoplethysmographic system taken on a patient with a stable blood analyte level. The emitters associated with channels 1 and 2 are inherently noisy sources by comparison with the light source used for channel 3, which is inherently much quieter. In this example, the light sources for channels 1 and 2 might be edge-emitting laser diodes and the light source for channel 3 might be an LED. The center wavelengths associated with these three channels in this sample of data are 660 nm, 800 nm, and 940 nm, respectively. Assuming that channel 1 and channel 2 are noise free, then a plot of successive dA values from channel 1, paired against those taken simultaneously from channel 2, would appear as shown in FIG. 5A. FIG. 5A shows a linear regression line drawn through the data and the slope of that line defined as "R". Using the actual data from channels 1 and 2 from FIG. 4, however, generates the results shown in FIG. 5B. As is obvious from the plot, the data are highly scattered. The regression line is very inaccurate; in fact, for this example it has a slightly negative slope. An O2Hb value calculated from this slope would be in error by more than 20%. So although the waveforms shown in FIG. 4 are still recognizable as photoplethysmographic waveforms, the saturation values that would be generated from data this noisy would be clinically useless.

FIG. 6A shows how this invention functions. In this plot the dAs from channel 1 are calculated from the noisy data shown in FIG. 4, but the dAs for channel 2 are calculated from a quiet version of the data shown in FIG. 4 for channel 2. Thus there is still a great deal of scatter in the data but the noise in these data is in the Y-axis direction only, as the dA2 data are essentially quiet. Regression analysis minimizes the sum of the squared deviation of the distance from the regression line in the selected direction. By performing a linear regression of the Y-axis data on the X-axis data (or said another way, by regressing the dA1 data on the dA2 data), the noise in the Y-axis data (or the dA1 data) is minimized. This results in a regression slope that is a best mathematical estimate to the theoretically perfect slope shown in FIG. 5A. In fact, passing each of these slopes through the calibration curve shown in FIG. 3 results in a clinically insignificant error in O2Hb of only 0.13%.

In the preceding example, a quiet channel 2 was used both as the quiet channel, providing the noise free template for the noisy channel, as well as for calculation of the desired blood analyte, O2Hb. In this way channel 2 serves a dual role both as the noise free template and as one of the required wavelengths or spectral bands needed for O2Hb measurement. This reduces the total number of different channels or emitters needed, which can be helpful in reducing the product cost and complexity while still maintaining maximum accuracy.

In cases where two noisy emitters must be used, perhaps for their specific optical properties, a third, quiet channel can be introduced only to provide a clean waveform or template as a reference. Assume that channels 1 and 2 are required for the measurement of O2Hb, but that both signals originate from noisy sources. The resulting data are as shown in FIG. 4. In this case channel 3 can be utilized solely as a template to provide clean photoplethysmographic data. Plotting dA1 against dA2 results in the scatter plot shown in FIG. 6B (which is identical to the scatter plot shown in FIG. 5B.). In this case, however, the regression line and slope is obtained by first regressing channel 1 on channel 3 and separately regressing channel 2 on channel 3. Finally, the regression slope is obtained by taking a ratio of these two regression slopes. This is the regression slope shown in FIG. 6B. Once again, through the use of a quiet channel to provide a clean template, the final slope is nearly identical to the slope of the noise free version. This final slope results in a saturation error of just 0.81%, which is again well within clinically acceptable levels.

By first regressing Channel 1 on Channel 3 and separately regressing Channel 2 on Channel 3, the noise in both regressions is primarily in the Y-direction only. The regressions minimize this noise component and generate accurate slopes for these data sets. A ratio of these two regression slopes results in the correct slope for a noise free version of the Channel 1 data regressed on a noise free version of the Channel 2 data. If $R_{YX}$ is the slope resulting from the linear regression of Y on X, then the mathematical method used to obtain the slope shown in FIG. 6B can be expressed as shown in Equation 4.

$$R_{12} = \frac{R_{13}}{R_{23}} \qquad \text{Equation 4}$$

In the case expressed by Equation 4, the third channel is used only as a template for cleaning up the data in channel 1 and channel 2. It should be clear that channel 3 could also be used as one of the selected channels or emitters providing one of the required spectral bands.

While the differential absorption calculations described above are one way to calculate slope values and then analyte levels, many other techniques exist for extracting the analyte levels from the photoplethysmographic waveforms. Some techniques use only the peak and valley from each cycle of the waveform from each channel. While this technique is different from the one previously described, it still requires clean photoplethysmographic data to make accurate analyte measurements and again the apparatus and method of this invention still apply.

One can generate a noise free version of the noisy waveforms in a number of different ways as long as there is at least one quiet waveform collected simultaneously. One way to accomplish this is an extension of the methods described above. If the slope of the linear regression line between a noisy and a clean channel has been determined as previously described herein, then a mathematical transformation can map the clean photoplethysmographic waveform data into a clean version of the noisy channel data. On a point-by-point basis the photoplethysmographic data from the clean channel can be raised to the power of the slope value to create a clean version of the previously noisy waveform. This can be expressed mathematically as shown in Equation 5.

$$It'_Y(t) = It_X(t)^{R_{yx}}$$ Equation 5

In this equation, $It_K(t)$ is the transmitted intensity (or photoplethysmographic waveform data) at time t for Channel K. Channel X is assumed to be the quiet channel and channel Y is assumed to be the noisy channel. $It'_Y(t)$ in Equation 5 is then the cleaned up version of the previously noisy value for this point. The "prime" (') symbol denotes that the "cleaned up" data are not identical to $It_Y$. These "cleaned up" data will have a different scaling than the original noisy waveform from which it was derived (as well as having less noise). This difference in scaling will be a constant multiplier which will not affect the calculation of the regression slope and may therefore be ignored.

Figure 7:
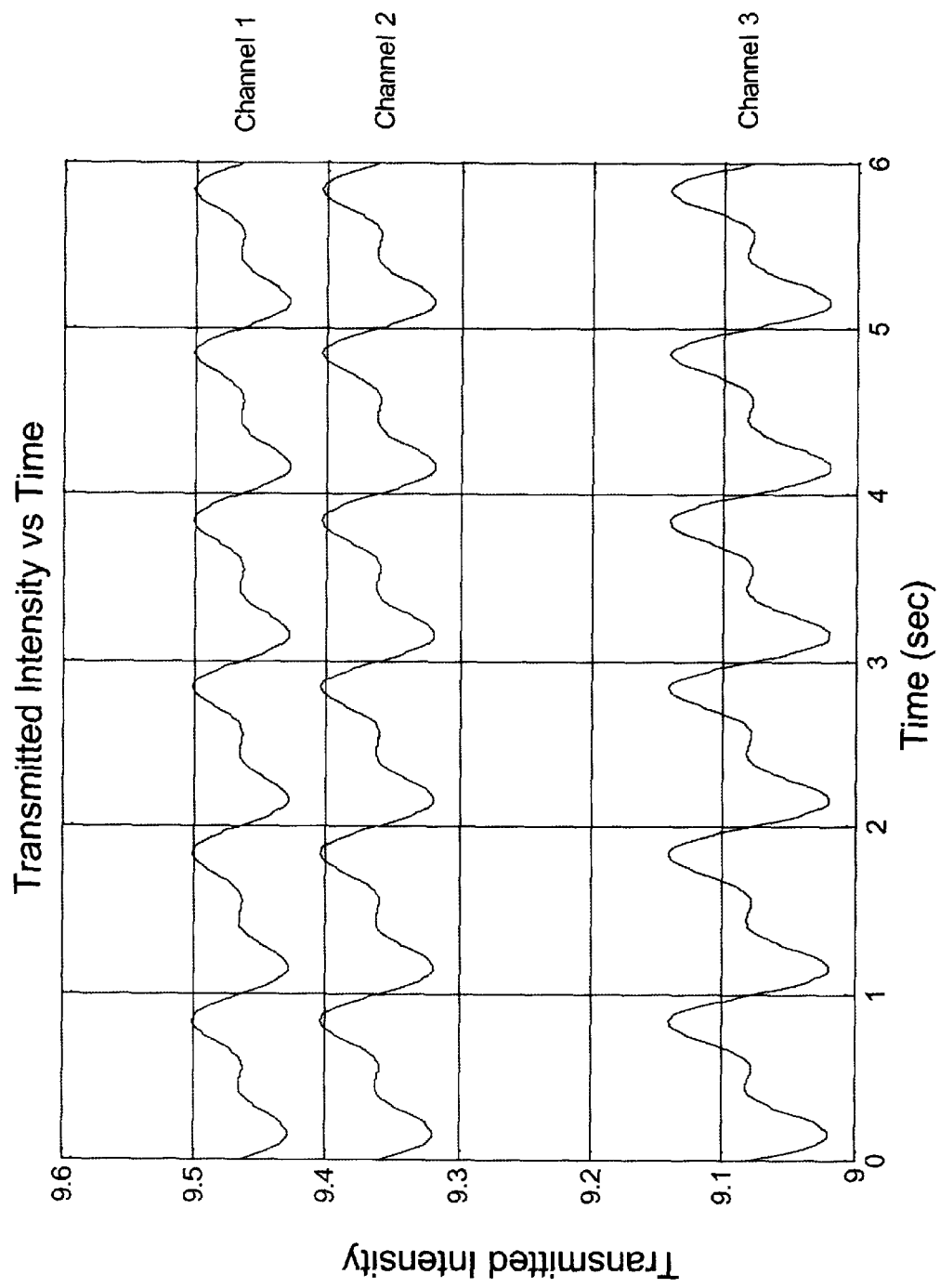
FIG. 7 is a graph of the same channels shown in FIG. 4 but "cleaned" using the apparatus and method of this invention. The result is three clean photoplethysmographic channels.

Once clean versions of the waveforms from the known noisy channels have been generated, these data can be used in any mathematical methodology for converting photoplethysmographic data into blood analyte measurements, or measurements of other hemodynamic parameters, with improved accuracy and precision of measurement. Using this methodology for cleaning up noisy waveforms, the data for channels 1 and 2 shown in FIG. 4 can be readily converted to clean waveforms as shown in FIG. 7. These clean waveforms are then used for measurement calculations.

The previous discussion of the invention has been presented for the purposes of illustration and description. The description is not intended to limit the invention to the form disclosed herein. Variations and modifications commensurate with the above are considered to be within the scope of the present invention. The embodiment described herein is further intended to explain the best mode presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

What is claimed is:

1. A photoplethysmographic measurement apparatus for measuring one or more blood analyte levels or one or more hemodynamic parameters in a tissue-under-test, comprising:
    a plurality of emitters, wherein at least one of said emitters is a quiet light source and at least one of said emitters is a noisy light source;
    an output aperture through which the light signals from the emitters are incident upon the tissue-under-test;
    a detector that receives a portion of said light signals exiting the tissue-under-test and converts said received light signals to electronic signals indicative of the said received light signals,
    a processor that utilizes said electronic signals, originating from at least one of said quiet light sources, to minimize the effects of the noise generated by at least one of said noisy light sources on the accuracy or precision of the measurements of said blood analyte levels or said hemodynamic parameters.

2. The apparatus of claim 1 wherein said at least one quiet light source comprises one or more light emitting diodes or one or more vertical cavity surface-emitting laser diodes.

3. The apparatus of claim 1 wherein said at least one noisy light source comprises one or more edge-emitting laser diodes.

4. The apparatus of claim 1 wherein said blood analyte levels comprises one or more of the levels of oxyhemoglobin, carboxyhemoglobin, methemoglobin, and reduced hemoglobin.

5. The apparatus of claim 1 wherein each of said emitters produces a light signal having a unique spectral content.

6. The apparatus of claim 1 wherein said processor utilizes said electronic signals from at least one of said quiet light sources in the generation of absorption measurements upon which to regress absorption measurements originating from said noisy light sources.

7. The apparatus of claim 6 in which said regressions yield one or more slope values to be used in the calculation of said measurements of said blood analyte levels or hemodynamic parameters.

8. The apparatus of claim 1 wherein said utilization of said electronic signals, originating from at least one of said quiet light sources, is as a template for the reduction of noise from said noisy light sources.

9. The apparatus of claim 8 wherein said template is an unscaled version of the waveshape of said electronic signals originating from any one of said noisy light sources.

10. The apparatus of claim 8 wherein said template is mathematically scaled and statistically fit to said electronic signals originating from any of said noisy light sources to provide a quiet version of the said electronic signals.

11. The apparatus of claim 10 wherein said quiet versions of said electronic signals are used for calculating said blood analyte levels or said hemodynamic parameters.

12. The apparatus of claim 1 wherein a plurality of spectral bands are required and wherein said one or more quiet light sources are utilized both for noise minimization of said electronic signals originating from said noisy light sources and as one or more of the required spectral bands for said measurements of said blood analyte levels or hemodynamic parameters.

13. In a photoplethysmographic measurement system, a method for measuring one or more blood analyte levels or one or more hemodynamic parameters in a tissue-under-test, said method comprising the steps of:
    providing a plurality of separate emitters, wherein at least one of said plurality of emitters is a quiet light source and at least one of said plurality of emitters is a noisy light source;
    applying light signals from said plurality of emitters to the tissue-under-test through an output aperture;
    receiving a portion of said light signals exiting the tissue-under-test and converting received light signals to electronic signals indicative of the said received light signals;
    processing said electronic signals originating from at least one of said noisy light sources based on the data in said electronic signals originating from at least one of said quiet light sources.

14. The method of claim 13 wherein said processing step further comprises the steps of:
    calculating a set of absorption values from said electronic signals originating from one of said noisy light sources;
    calculating a corresponding set of absorption values from said electronic signals originating from one of said quiet light sources;
    regressing the set of absorption values originating from said noisy light source on said corresponding set of absorption values originating from said quiet light source;

calculating said blood analyte levels or said hemodynamic parameters based on the results of said regression calculation.

15. The method of claim 13 wherein said processing step further comprises the steps of:
   curve fitting said electronic signal originating from one of said quiet light sources to said electronic signal originating from one of said noisy light sources;
   utilizing the curve fit version of the said electronic signal originating from one of said noisy light sources to calculate said blood analyte levels or said hemodynamic parameters based.

16. The method of claim 15 wherein said curve fitting step comprises scaling said electronic signal originating from one of said quiet light sources to provide a statistical best fit to said electronic signal originating from one of said noisy light sources.

17. The method of claim 13 wherein said quiet light sources consist of one or more light emitting diodes or one or more vertical cavity surface-emitting laser diodes.

18. The method of claim 13 wherein said noisy light sources consist of one or more edge-emitting laser diodes.

19. The method of claim 13 wherein said blood analyte levels consist of one or more of the levels of oxyhemoglobin, carboxyhemoglobin, methemoglobin and reduced hemoglobin.

20. The method of claim 13 wherein each of said emitters produces a light signal having a unique spectral content.

21. The method of claim 13 wherein a plurality of spectral bands are required and wherein said quiet light sources are utilized both for minimization of noise originating from said noisy light sources and as one or more of the required spectral bands for said measurements of said blood analyte levels or hemodynamic parameters.

* * * * *

UNITED STATES PATENT AND TRADEMARK OFFICE
CERTIFICATE OF CORRECTION

PATENT NO. : 6,754,515 B1
DATED : June 22, 2004
INVENTOR(S) : Jonas Alexander Pologe It is certified that error appears in the above-identified patent and that said Letters Patent is hereby corrected as shown below:

Column 1,
Line 3, insert the following:
--  STATEMENT OF GOVERNMENT INTEREST
This invention was made with government support under R44 HL073518 awarded by National Institutes of Health. The government has certain rights in the invention. --.

Signed and Sealed this

Eleventh Day of April, 2006

JON W. DUDAS
*Director of the United States Patent and Trademark Office*